United States Patent [19]

Galliani et al.

[11] Patent Number: 4,535,090
[45] Date of Patent: Aug. 13, 1985

[54] 3,5-DIPHENYL-1H-1,2,4-TRIAZOLES PHARMACEUTICAL COMPOSITIONS AND USES

[75] Inventors: Giulio Galliani, Monza; Amedeo Omodei-Salé, Voghera; Pietro Consonni, Milan; Alessandro Assandri, Mariano Comense, all of Italy

[73] Assignee: Gruppo Lepetit S.p.A., Italy

[21] Appl. No.: 434,451

[22] Filed: Oct. 15, 1982

[30] Foreign Application Priority Data

Oct. 20, 1981 [GB] United Kingdom ............... 8131657

[51] Int. Cl.³ ............... A61K 31/41; C07D 249/10; C07D 405/10
[52] U.S. Cl. ............... 514/383; 544/63; 514/843; 548/262; 549/308; 549/310; 549/441; 549/442; 560/106
[58] Field of Search ............... 548/262; 424/269

[56] References Cited

FOREIGN PATENT DOCUMENTS 2034710 6/1980 United Kingdom ............... 548/262
2039887 8/1980 United Kingdom ............... 548/262
1579352 11/1980 United Kingdom ............... 548/262

*Primary Examiner*—Alton D. Rollins
*Attorney, Agent, or Firm*—William J. Stein; Stephen L. Nesbitt

[57] ABSTRACT

3,5-diphenyl-1H-1,2,4-triazoles with contragestational activity of the following formula

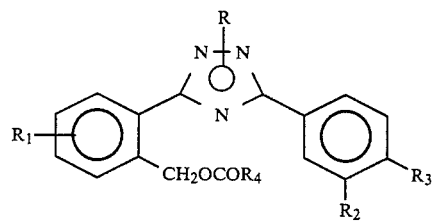

wherein R may be located on one or the other of the two adjacent nitrogen atoms and may represent hydrogen or a group $R_5CO-$ wherein $R_5$ is an aliphatic saturated or unsaturated hydrocarbyl containing from 1 to 20 carbon atoms, $R_1$, $R_2$ and $R_3$, each independently are selected from hydrogen, lower alkyl and lower alkoxy or $R_2$ and $R_3$ together may represent a methylenedioxy group, and $R_4$ is an aliphatic saturated or unsaturated hydrocarbyl group of from 1 to 20 carbons, with the proviso that when R is hydrogen or an $R_5CO-$ group wherein $R_5$ contains 4 or less carbon atoms, $R_4$ must contain 5 or more carbons.

These compounds have proven to be highly effective in terminating pregnancy in several animal species after a single parenteral injection.

4 Claims, No Drawings

3,5-DIPHENYL-1H-1,2,4-TRIAZOLES PHARMACEUTICAL COMPOSITIONS AND USES

The present invention relates to a new class of 3,5-diphenyl-1H-1,2,4-triazoles with contragestational activity, to the pharmaceutical compositions containing them and to the process for their preparation.

More particularly the compounds which are the first object of the present invention have the following general formula

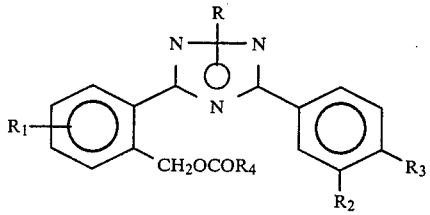

wherein R may be located on one or the other of the two adjacent nitrogen atoms and may represent hydrogen or a group $R_5CO-$ wherein $R_5$ is an aliphatic, saturated or unsaturated, hydrocarbyl containing from 1 to 20 carbon atoms, $R_1$, $R_2$, and $R_3$, each independently, are selected from hydrogen, lower alkyl and lower alkoxy or $R_2$ and $R_3$ taken together may represent a methylenedioxy group, and $R_4$ is an aliphatic, saturated or unsaturated, hydrocarbyl group of from 1 to 20 carbon atoms, with the proviso that when R is hydrogen or an $R_5-CO$ group wherein $R_5$ is an aliphatic, saturated or unsaturated, hydrocarbyl of 4 or less carbon atoms, $R_4$ must contain 5 or more carbons.

For the scope of the present invention the term "aliphatic, saturated or unsaturated, hydrocarbyl", designates straight or branched alkyl, alkenyl and alkynyl groups, which may contain more than one double or triple bond. The terms "lower alkyl" and "lower alkoxy" refer to straight or branched alkyl and alkoxy groups having 1,2,3 or 4 carbon atoms.

A preferred group of compounds of the present invention comprises those compounds of formula I wherein R may be located on one or the other of the two adjacent nitrogen atoms and may represent hydrogen or an $R_5-CO$ group wherein $R_5$ is an aliphatic saturated hydrocarbyl group of from 1 to 6 carbon atoms, $R_1$ is hydrogen, $R_2$ is a lower alkoxy group, $R_3$ is selected from hydrogen, lower alkyl or lower alkoxy, or $R_2$ and $R_3$ taken together represent a methylenedioxy group, and $R_4$ is an aliphatic saturated hydrocarbyl group of 5 to 20 carbon atoms.

A most preferred group of compounds of the present invention comprises those compounds of formula I wherein R is hydrogen, $R_1$ is hydrogen, $R_2$ is methoxy or ethoxy, $R_3$ is hydrogen, methyl, methoxy, or ethoxy, or $R_2$ and $R_3$ taken together represent a methylenedioxy group, and $R_4$ is an aliphatic saturated hydrocarbyl group of 8 to 14 carbon atoms.

The compounds of the present invention have proven to be highly effective agents for the termination of pregnancy in several animal species after a single parenteral injection.

3,5-Diphenyl-triazoles with contragestational activity are already known from the prior-art, more particularly Belgian Pat. No. 866,728 describes a class of 3,5-disubstituted-1,2,4-triazoles of the formula

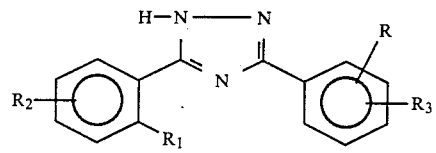

characterized by the presence of a lower alkyl group at the ortho position of one of the phenyl rings ($R_1$ is defined as a $(C_1-C_4)$alkyl group).

European patent application publication No. 11,129 describes 1,2,4-triazole derivatives of the formula

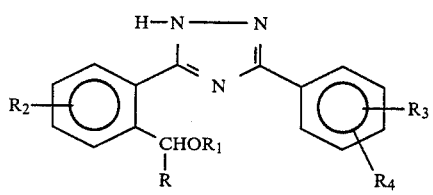

wherein R represents hydrogen or methyl and $R_1$ stands for hydrogen or $(C_1-C_4)$alkyl or R and $R_1$ taken together may represent an additional bond between the carbon and the oxygen atoms.

Finally, Belgian Pat. No. 879,732 describes a class of compounds of the formula

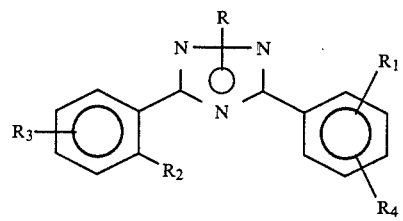

wherein, inter alia, R represents hydrogen or a group $R_5-CO$ wherein $R_5$ may represent a $(C_1-C_4)$alkyl, $(C_2-C_4)$alkenyl or $(C_2-C_4)$alkynyl group and $R_2$ stands for the group

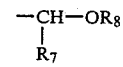

wherein $R_7$ is hydrogen or methyl and $R_8$ is $R_5-CO$.

In the above references, pharmacological data showing the high contragestational effectiveness of representative compounds of the above classes, following multiple dose treatments (5 days), were reported. However, the compounds described in the above patents and patent application, when tested according to a single dose treatment schedule, resulted in low activity, requiring for pregnancy arrest doses much higher than the present compounds.

The compounds of the present invention make up a class of new non-hormonal, non-prostaglandin like, post-coital, post-implantation antifertility agents particularly useful for terminating pregnancy in mammals following a single dose treatment.

They were found to be effective at very low doses, in some instances ranging between one twentieth and one thirtieth of the dose of prior-art compounds required in the same test.

The pregnancy-terminating activity of the compounds of the present invention has been assessed by carrying out experiments in rats. In particular, female Sprague Dawley rats weighing 200–230 g were mated and the presence of sperm in the vagina was taken as evidence of mating. The day the sperm was detected, was considered day one of pregnancy. Pregnancy was later confirmed at the time of autopsy by the presence of implantation sites in the uterus.

Test compounds dissolved in sesame oil containing 20% benzyl benzoate (or suspended if insoluble), were administered subcutaneously, in a single injection, on day 7 of gestation. The animals were then autopsied on day 16 of pregnancy and the uteri were examined for evidence of pregnancy (implantation sites, fetal resorption or live fetuses), hemorrage, and evidence of abnormalities of the uterus, placenta or fetuses.

The compounds were tested at different doses in order to study the dose-activity relationship and their activity has been expressed in following Table I as $ED_{50}$ values. These values identify the dose levels which terminate pregnancy (absence of live fetuses) in 50% of the treated animals. For comparison purposes, below the dashed line, the $ED_{50}$ of some related triazoles previously disclosed (Belgian Pat. Nos. 866,728 and 879,732 and European patent application publication No. 11,129), are reported.

TABLE I

PREGNANCY TERMINATION ACTIVITY IN RATS AFTER A SINGLE SUBCUTANEOUS INJECTION AT DAY 7 OF GESTATION

| Compound of Example No. | $ED_{50}$ mg/kg |
| --- | --- |
| 1 | 13 |
| 2 | 2 |
| 3 | 4 |
| 4 | 2 |
| 6 | 2 |
| 7 | 2 |
| 8 | 10 |
| 9 | 7 |
| 10 | 4 |
| 11 | 8 |
| 5-(2-Hydroxymethylphenyl)-3-(3-methoxyphenyl)-1H—1,2,4-triazole described in example 1 of European patent application Publication No. 11,129 | 40 (given suspended instead of dissolved |
| 5-(2-Ethylphenyl)-3-(3-methoxyphenyl)-1H—1,2,4-triazole described in example 13 of Belgian patent 866,728 | 35 |
| 5-(2-Acetyloxymethylphenyl)-3-(3-methoxyphenyl)-1H—1,2,4-triazole described in example 24 of Belgian patent 879,732 | 50 |

For use in terminating pregnancy, the compounds of the present invention are embodied into injectable dosage forms and administered subcutaneously or intramuscularly. Such compositions are formulated using a non-aqueous vehicle. As an example oils of vegetable origin or fat esters such as sesame oil, corn oil, peanut oil, cotton seed oil, and ethyl oleate can suitably be employed.

Other oily vehicles may as well be used provided that they are safe in the volume administered and do not interfere with the therapeutic efficacy of the preparation.

As known to the art, these preparations may also contain antimicrobial agents, to prevent growth of microorganisms in the preparation, and antioxidants, essentially to prevent the development of rancidity of the oily vehicle. These dosage forms in general contain from 1 to 10% (w/v) of active principle, where the optimum ratio depends on the selected dose and the species and size of the animal to be treated.

The compounds of the present invention can be prepared starting from the corresponding 2-hydroxymethylphenyl derivatives of formula II

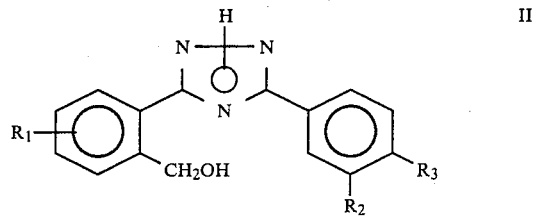

through acylation procedures. More particularly, when compounds of formula I are desired wherein R is a group $R_5$—CO wherein $R_5$ has the same meaning as $R_4$, the acylation reaction is preferably carried out by treating the 2-hydroxymethylphenyl derivative II with an excess over the stoichiometric amount of a suitably selected acylating agent of formula $R_4$—COX wherein X is a halogen atom, preferably chlorine, or the group $R_4$—CO—O—.

The reaction is carried out in the presence of an acid binding agent, e.g. a tertiary organic nitrogen base, such as for instance, trimethylamine, triethylamine, pyridine, pycoline, collidine and analogs, at a temperature which may vary from room temperature to the reflux temperature of the reaction mixture. The reaction may run either in the absence or in the presence of an organic solvent. If an organic solvent is employed, preferred organic solvents are selected from dioxane, tetrahydrofuran, methylenechloride, 1,2-dichloroethane, benzene and the like. It has also been observed that the tertiary base may act as the solvent as well.

If desired, the N,O-diacyl derivatives thus obtained, may be subjected to a mild alkaline hydrolysis thus yielding the corresponding compounds I wherein R is hydrogen.

In actual practice, the hydrolysis is carried out by contacting a molar proportion of the predetermined triazole substrate with about two molar equivalents of a mild alkaline agent, e.g. diluted aqueous sodium or potassium bicarbonate, in the presence of an organic solvent, e.g. dioxane, tetrahydrofuran and analogs, at a temperature comprising between room temperature and the boiling temperature of the reaction mixture.

Alternatively, compounds of formula I wherein R is hydrogen may also be prepared by using only one molar proportion of the acylating agent per mole of starting 2-hydroxymethylphenyl triazole and optionally transforming the small amount of N,O-diacyl derivative which forms, into the desired O-acyl derivative by transesterification with methanol and alkali metal carbonates. However, a preferred method for selectively acylating the hydroxymethyl group consists in reacting the starting compound of formula II with one molar proportion or a slight excess of the suitably selected acylating agent and a tertiary organic nitrogen base, as seen above, in the presence of catalytic amounts of 4-dimethylamino-pyridine.

Compounds of formula I wherein R is a group $R_5$—CO wherein $R_5$ is different from $R_4$ are then prepared, if desired, from the corresponding compounds of formula I wherein R is hydrogen, prepared as described above, by following the general method described before but using, as the acylating agent, a suitably selected acyl halide or anhydride of formula $R_5$—COY wherein Y stands for a halogen atom or the group —O—CO—$R_5$. Also in this case the reaction requires the presence of an acid binding agent as seen above, while the presence of a solvent is not strictly necessary. However, when a solvent is employed it is generally selected from anhydrous inert organic solvents, e.g. benzene, toluene, methylene chloride, dioxane, tetrahydrofuran, or mixtures thereof.

According to what is known from the chemical literature (see Kubota and Uda, Chem. Pharm. Bull. 23(5), 955 (1975), the 3,5-disubstituted 1,2,4-triazoles of formula I wherein R is hydrogen, are to be regarded as a mixture of two tautomeric forms, i.e. those in which the hydrogen atom is located on one or the other of the two adjacent nitrogen atoms. At ordinary temperature, these forms are in a state of dynamic equilibrium, i.e. they rapidly exchange into each other, and, depending on the nature of the substituents at the 3 and 5 positions, one form may predominate over the other one. However, for numbering purposes, in these N-unsubstituted triazoles the phenyl group bearing the —$CH_2OCOR_4$ substituent is conventionally assigned the position 5 and the other the position 3. When, according to the acylation procedures seen above, compounds of formula I wherein R is other than hydrogen are prepared, they may be obtained as single compounds wherein the substituent R is located on one only of the two adjacent nitrogen atoms, as well as a mixture of the two possible isomers. In any case, if a mixture of isomers, which possesses the same degree of anti-reproductive activity of the single compounds is obtained, this can be separated into the single components by means of known chemico-physical techniques. An example illustrating the way a mixture can be resolved into the single components is fractional crystallization, which is based on the different solubilities of the components in a predetermined solvent at different temperatures. Suitable solvents which may be advantageously employed in this method are selected from hexane, ethyl acetate, ($C_1$–$C_4$) alkyl ethers, methylene chloride, light petroleum and mixtures thereof. A further illustrative example is represented by the column chromatography on non-acid, buffered supports, e.g. pH 7 buffered silica-gel. A third illustrative example is represented by the preparative high pressure liquid chromatography (preparative HPLC), which is carried out by employing suitable columns, as an example silica-gel esterified with octylsilane or octadecylsilane. Other obvious procedures useful for resolving a mixture of isomers into the single components are intended to fall within the scope of the invention.

In numbering these N-substituted triazoles, the nitrogen atom bearing the substituent R is conventionally assigned the number 1 and the adjacent nitrogen atom the number 2. The 2-hydroxymethylphenyl derivatives of formula II, used as starting materials in the process of the present invention, can be prepared by different methods generally known in literature. As an example the method described in European patent application publication No. 11,129 can suitably be employed.

This method consists in the rearrangement of hydrazones of substituted benzaldehydes with 4-hydrazino-1H-2,3-benzoxazines of formula III

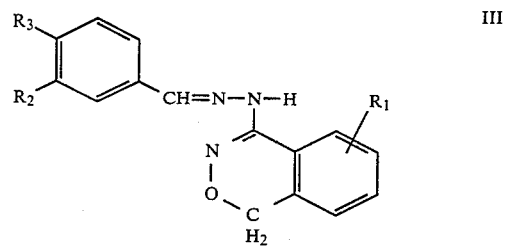

wherein $R_1$, $R_2$, and $R_3$ are as defined above.

This rearrangement simply occurs by refluxing the hydrazone III in a high boiling inert organic solvent, such as for instance, xylene, N,N-dimethylformamide, and halogenated aromatic hydrocarbons, for about 30 minutes and then recovering the compound II by filtration. Another suitable method for the preparation of the 2-hydroxymethylphenyl derivatives of formula II, consists in the oxidation of the corresponding 2-methylphenyl triazoles, either directly to the alcohol II or to the corresponding carboxylic acid followed by a reduction of this latter to the alcohol II.

In the former case, ceric ammonium nitrate or silver (II) oxide are the oxidizing agents which may be suitably employed, while in the latter, the oxidative step is carried out with any of the several oxidizers known in the art to transform a methyl group on an aromatic ring to a —COOH group, such as permanganate, nitric acid, and dichromate, and the reductive step is easily performed with a metal hydride.

Alternatively, the starting compounds of formula II can be prepared by following the process summarized in the following scheme:

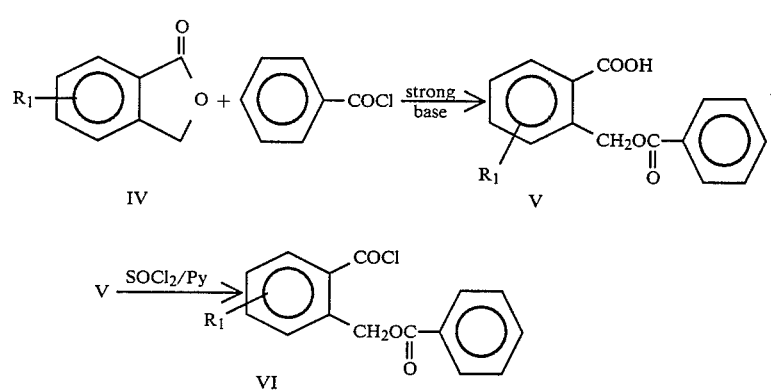

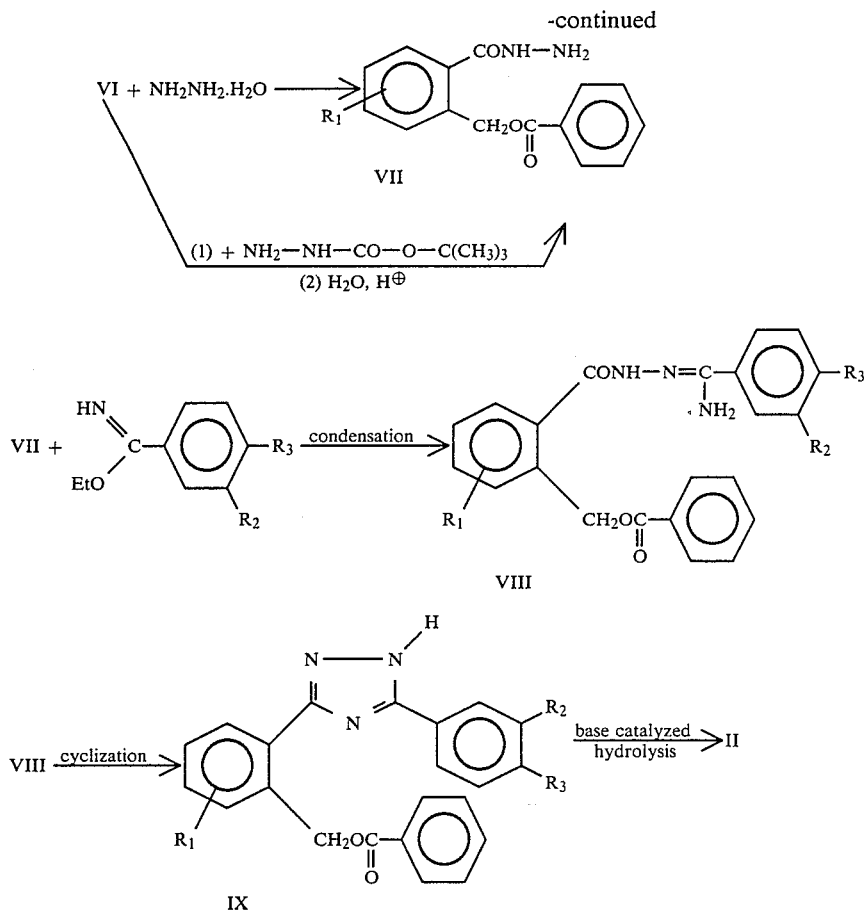

The first steps of the above process consist in the opening of the phthalide derivative IV with benzoyl chloride followed by the transformation of the acid V into the corresponding chloride VI by reaction with thionyl chloride in an inert high boiling organic solvent, in the presence of pyridine.

The acid chloride VI is then transformed into the corresponding hydrazide VII either directly by reaction with hydrazine hydrate, or by reaction with t-butylcarbazate followed by acid hydrolysis. Condensation of the obtained hydrazide with a suitable selected imino-ester yields the benzamidrazone VIII which easily cyclizes, by heating in an inert high boiling organic solvent and distilling the water which forms, to the corresponding benzoyloxymethylphenyl-triazole IX which is finally subjected to saponification giving the desired hydroxymethylphenyl-triazole II.

The following examples illustrate the way of making the compounds of the invention and describe in detail some of them, but in no way do they have to be construed as a limitation to the scope of the invention itself.

EXAMPLE 1

3-(3-methoxyphenyl)-5-(2-octanoyloxymethylphenyl)-1H-1,2,4-triazole

A solution of octanoyl chloride (4.25 ml, 25 mmole) in dioxane (10 ml) is added dropwise during ten minutes into a stirred suspension of 5-(2-hydroxymethylphenyl)-3-(3-methoxyphenyl)-1H-1,2,4-triazole (2.81 g, 10 mmole) and triethylamine (4.2 ml, 30 mmole) in dioxane (50 ml). After 1 hour, 8% NaHCO$_3$ (50 ml) is added and the reaction mixture is heated to 50° C. for two hours, cooled to room temperature, diluted with water (60 ml) and extracted with methylene chloride. The organic extracts are washed with water, dried over Na$_2$SO$_4$ and concentrated to dryness yielding a raw residue which is purified by silica-gel column chromatography eluting with a mixture 0% to 10% ethyl acetate in toluene and crystallized from isopropyl ether/petroleum ether. Yield: 56.5%. M.p. 61° C. and 87° C. (as a mixture of crystal forms).

EXAMPLE 2

5-(2-dodecanoyloxymethylphenyl)-3-(3-methoxyphenyl)-1H-1,2,4-triazole

The compound of the title has been prepared by following the same procedure described in the foregoing example but using dodecanoyl chloride instead of octanoyl chloride and a mixture of ethyl ether/petroleum ether instead of isopropyl ether/petroleum ether as the crystallization solvent. Yield: 59.5%. M.p. 45° C. and 57° C. (as a mixture of crystal forms).

EXAMPLE 3

3-(3-ethoxyphenyl)-5-(2-octanoyloxymethylphenyl)-1H-1,2,4-triazole

A mixture of 5-(2-hydroxymethylphenyl)-3-(3-ethoxyphenyl)-1H-1,2,4-triazole (2.36 g, 8 mmole) and octanoyl chloride (1.6 ml, 9.4 mmole) in 1,2-dichloroethane (24 ml) is heated to the reflux temperature with stirring. When the reaction, which is followed by thin layer chromatography (silica-gel plates, toluene: ethyl acetate 1:1), is complete, the reaction mixture is cooled to room temperature and methanol (8 ml) is added. Then an excess of NaHCO$_3$ (1.21 g, 14.4 mmole) is added to neutralize the hydrochloric acid formed during the reaction, followed, after a few minutes, by anhydrous K$_2$CO$_3$ (0.062 g, 0.45 mmole). When the partial transesterification of the N,O-diacyl derivative into the desired monoacyloxy one is complete, the reaction mixture is diluted with water (20 ml), the organic phase is separated and the aqueous one is extracted with methylene chloride (2×10 ml). The organic extracts are combined, washed with water, dried over Na$_2$SO$_4$ and concentrated to dryness giving a row residue which is purified by crystallization from hexane. Yield: 61%. M.p. 87°–89° C.

The following compounds have been prepared according to the method described in the foregoing example but using the reactants indicated between parenthesis:

EXAMPLE 4

5-(2-decanoyloxymethylphenyl)-3-(3-methoxyphenyl)-1H-1,2,4-triazole (from 5-(2-hydroxymethylphenyl)-3-(3-methoxyphenyl)-1H-1,2,4-triazole and decanoyl chloride).Yield: 35%. M.p. 88°–90° C. (from ethyl ether/petroleum ether).

EXAMPLE 5

3-(3,4-dimethoxyphenyl)-5-(2-octanoyloxymethylphenyl)-1H-1,2,4-triazole (from 5-(2-hydroxymethylphenyl)-3-(3,4-dimethoxyphenyl)-1H-1,2,4-triazole and octanoyl chloride).Yield: 75.1%. M.p. 76° C. and 85° C. (from ethyl ether/petroleum ether).

EXAMPLE 6

5-(2-dodecanoyloxymethylphenyl)-3-(3,4-dimethoxyphenyl)-1H-1,2,4-triazole (from 5-(2-hydroxymethylphenyl)-3-(3,4-dimethoxyphenyl)-1H-1,2,4-triazole and dodecanoyl chloride).Yield: 63.5%. M.p. 89°–91° C. (from ligroine).

EXAMPLE 7

5-(2-decanoyloxymethylphenyl)-3-3-ethoxyphenyl)-1H-1,2,4-triazole

Triethylamine (3.4 ml, 24 mmole) and 4-dimethylaminopyridine (0,275 g, 0.22 mmole) are added to a suspension of 5-(2-hydroxymethylphenyl)-3-(3-ethoxyphenyl)-1H-1,2,4-triazole (6.5 g, 22 mmole) in 1,2-dichloroethane (40 ml). Then a solution of decanoyl chloride (5.3 ml, 27 mmole) in 1,2-dichloroethane (10 ml) is added dropwise to the above mixture with stirring. The reaction mixture is then allowed to stand at room temperature for one night, washed with water (35 ml) first, then with 3% HCl (two 35-ml portions) and finally with water up to neutral reaction. The organic solution is then dried over Na$_2$SO$_4$ and concentrated to dryness yielding a raw residue which is crystallized from hexane/ethyl ether 5/1. M.p. 81°–83° C. Yield: 85.9%.

By following the same procedure described above but using proper reactants, indicated between parenthesis, the following compounds have been prepared:

EXAMPLE 8

5-(2-decanoyloxymethylphenyl)-3-(3,4-dimethoxyphenyl)-1H-1,2,4-triazole (from 5-(2-hydroxymethylphenyl)-3-(3,4-dimethoxyphenyl)-1H-1,2,4-triazole and decanoyl chloride). Yield: 67.7%. M.p. 83°–86° C. (from ligroine).

EXAMPLE 9

3-(3-ethoxyphenyl)-5-(2-hexanoyloxymethylphenyl)-1H-1,2,4-triazole (from 3-(3-ethoxyphenyl)-5-(2-hydroxymethylphenyl)-1H-1,2,4-triazole and hexanoyl chloride). Yield: 69.5%. M.p. 93°–95° C. (from ethyl ether/petroleum ether).

The preparation of the compounds described in examples 3,4, and 6 has been repeated by following the procedure described in example 7 with the following percent yields: 85.7, 73.3, and 84% respectively.

EXAMPLE 10

1-acetyl-3(5)-(2-decanoyloxymethylphenyl)-5(3)-(3,4-dimethoxyphenyl)-1H-1,2,4-triazole A solution of 5-(2-decanoyloxymethylphenyl)-3-(3,4-dimethoxyphenyl)-1H-1,2,4-triazole (0.4 g, 0.86 mmole) described in example 9, and acetic anhydride (0.097 ml, 1.02 mmole) in benzene (10 ml) is heated to the reflux temperature for three hours. Acetic anhydride (two 0.0485 ml and one 0.025 ml portions) is added at two hour intervals while the reaction mixture is heated to reflux for an overall reaction time of 10 hours. The reaction mixture is then concentrated to dryness, taken up with benzene and concentrated again. The raw residue is triturated with hexane, recovered by filtration and dried under vacuum yielding 0.2 g of the compound of the title. M.p. 57° C.

EXAMPLE 11

1-hexanoyl-3(5)-(2-hexanoyloxymethylphenyl)-5(3)-(3-methoxyphenyl)-1H-1,2,4-triazole A solution of 5-(2-hydroxymethylphenyl)-3-(3-methoxyphenyl)-1H-1,2,4-triazole (0.281 g, 1 mmole), triethylamine (0.28 ml, 2 mmole), and hexanoylchloride (0.42 ml, 3 mmole) in methylene chloride (15 ml) is stirred at room temperature for 1 hour, then a few crystals of dimethylaminopyridine are added. After 30 minutes the reaction mixture is diluted with methylene chloride (10 ml), washed with water first (two 10-ml portions), dried over sodium sulfate and concentrated to dryness. To the obtained oily residue (0.360 g) petroleum ether is added and the solid which forms, which consists of the mono-acyl derivative, is separated by filtration, while the filtrate which contains the di-acyl derivative is concentrated to dryness. This operation is repeated three times yielding 0.120 g of the compound of the title, as an oily product.

EXAMPLE 12

1-dodecanoyl-3(5)-(2-dodecanoyloxymethylphenyl)-5(3)-(3,4-dimethoxyphenyl)-1H-1,2,4-triazole The compound of the title has been prepared by following substantially the same procedure described in the foregoing example but using dodecanoyl chloride instead of hexanoyl chloride. Once the oily residue is obtained, it is applied to a silica-gel column prepared in toluene. The column is developed with a mixture toluene/ethyl acetate wherein the percentage of ethyl acetate increases, starting from zero, by 2% every 300 ml. The compound of the title is recovered by collecting the 10% ethyl acetate fractions. M.p. 50°–53° C. (from ligroine).

Preparation of the starting compounds of formula II:

(A) 5-(2-hydroxymethylphenyl)-3-(3-methoxyphenyl)-1H-1,2,4-triazole

A suspension of 16 g of 4-[2-(3-methoxybenzyliden)-hydrazino]-1H-2,3-benzoxazine in 160 ml of anhydrous xylene is refluxed for 45 minutes and then cooled to about 0° C. The solid which precipitates is recovered by filtration and recrystallized from ethanol yielding 14.7 g of the compound of the title. M.p. 157°–59° C.

(B) 5-(2-hydroxymethylphenyl)-3-(3-methoxyphenyl)-1H-1,2,4-triazole (1) 2-benzoyloxymethylbenzoic acid (V:$R_1=H$)

Phthalide (134 g, 1 mole) is dissolved in 20% NaOH (715 ml, 3.58 mole) by heating the mixture to about 60° C. The obtained solution is diluted with water (750 ml) and ice (5 kg). Benzoyl chloride (151 ml, 1.3 mole) is added in 10 minutes with vigorous stirring and about 1 hour later the pH of the reaction mixture is brought to 2.5 by the addition of 10% HCl (750 ml). The solid which is collected under vacuum filtration is washed carefully with warm water (4×1500 ml) and crystallized from ethanol/water 7/3 (800 ml), yielding 98.2 g of 2-benzoyloxymethylbenzoic acid. M.p. 118°–124° C.

(2) 2-benzoyloxymethylbenzoic acid chloride (VI:$R_1=H$)

Anhydrous pyridine (24.4 ml, 0.3 mole) is added to a suspension of 2-benzoylmethylbenzoic acid (76.9 g, 0.3 mole) in anhydrous toluene (225 ml). Then thionyl chloride (323 ml, 4.5 mole) is added in 30 minutes and the reaction mixture is gradually heated to 80° C. After 20 minutes at this temperature, the reaction mixture is concentrated to dryness under vacuum and the solid residue is extracted with anhydrous toluene at 60° C. (two 500-ml plus two 250-ml portions). After evaporating the organic solvent, the solid is triturated with hexane (250 ml) yielding 78.2 g of the acid chloride VI. M.p. 51°–52° C.

(3) 2-benzoyloxymethylbenzoyl hydrazide (VII: $R_1=H$)

(a) A solution of 2-benzoyloxymethylbenzoyl chloride (79.7 g, 0.29 mole) in methylene chloride (230 ml) is slowly added to a stirred solution of 98% hydrazine hydrate (58 ml, 1.16 mole) in 95% ethanol (230 ml) cooled to 0° C.

The obtained reaction mixture is stirred at room temperature for two hours, then the lower phase is separated, and the upper one is extracted with methylene chloride (two 50-ml portions). The combined methylene chloride extracts are washed with an aqueous solution saturated with NaCl, dried over $Na_2SO_4$ and concentrated to dryness. The obtained residue is crystallized from methylene chloride/isopropyl ether yielding 58.4 g of 2-benzoyloxymethylbenzoyl hydrazide. M.p. 128°–30° C.

(b) A solution of 2-benzoyloxymethylbenzoyl chloride (2.75 g, 0.01 mole) in methylene chloride (5 ml) is added dropwise into a solution of t-butylcarbazate (1.32 g, 0.01 mole) and triethylamine (2.12 ml, 0.015 mole) in methylene chloride (10 ml) and the reaction mixture is stirred at room temperature for two hours. 37% HCl (8.8 ml) and methylene chloride (10 ml) are added and the mixture is stirred for an additional hour at room temperature. Then the pH of the reaction mixture is brought to 8 by the addition of 30% NaOH, the organic phase is separated and the aqueous one is extracted with methylene chloride (2×10 ml). The organic extracts are combined, washed, dried over $Na_2SO_4$ and concentrated to dryness. The residue thus obtained is crystallized from a mixture of methylene chloride/isopropyl ether 1:2 (60 ml) yielding 1.86 g of pure 2-benzoyloxymethylbenzoyl hydrazide. M.p. 132°–33° C.

(4) 2-benzoyloxymethylbenzoic acid [amino(3-methoxyphenyl)methyl]hydrazide (VIII: $R_1=R_3=H$, $R_2=-OCH_3$)

A solution of 2-benzoyloxymethylbenzoyl hydrazide (2.97 g, 11 mmole) and 3-methoxybenzimidic acid ethyl ester (2.17 g, 12.1 mmole) in sym-dichloroethane (30 ml) is heated on an oil bath to 90° C. After 1½ hour, the temperature is increased to 110° C. and about 15 ml of the solvent is distilled. The reaction mixture is then cooled to room temperature, and the precipitate is recovered by filtration, washed with methylene chloride and dried under vacuum yielding 3.8 g of benzamidrazone VIII. M.p. 173°–74° C.

(5) 3-(2-benzoyloxymethylphenyl)-5-(3-methoxyphenyl)-1H-1,2,4-triazole (IX: $R_1=R_3=H$, $R_2=-OCH_3$)

A suspension of the benzamidrazone obtained in paragraph (4) above, in ten volumes of xylene is heated to the reflux temperature while water which forms is separated as a binary azeotrope. After one hour the reaction mixture is cooled to room temperature and the precipitate is recovered by filtration and dried under vacuum yielding 3.05 g of 3-(2-benzoyloxymethylphenyl)-5-(3-methoxyphenyl)-1H-1,2,4-triazole. M.p. 128°–130° C.

(6) 3-(2-hydroxymethylphenyl)-5-(3-methoxyphenyl)-1H-1,2,4-triazole (II: $R_1=R_3=H$, $R_2=-OCH_3$)

A solution of 3-(2-benzoyloxymethylphenyl)-5-(3-methoxyphenyl)-1H-1,2,4-triazole (37.1 g, 0.1 mole) in 10% NaOH (160 ml) and 95% ethanol (240 ml) is heated to 70° C. for one hour, then ethanol is distilled under vacuum and the reaction mixture is diluted with water (240 ml) and decolorized with activated carbon. The filtrate is brought to pH 8 by the addition of 10% HCl and stirred at room temperature for a few hours. The solid which separates is recovered by filtration and dried under vacuum yielding 24.2 g of 3-(2-hydroxymethylphenyl)-5-(3-methoxyphenyl)-1H-1,2,4-triazole. M.p. 155°–56° C.

The following compounds of formula II are prepared by following the same procedures described above under (B), but using the proper substituted benzimidic acid ethyl ester instead of 3-methoxybenzimidic acid ethyl ester in step 4.

(C) 3-(3-ethoxyphenyl)-5-(2-hydroxymethylphenyl)-1H-1,2,4-triazole (M.p. 157°–59° C.)

(D) 5-(2-hydroxymethylphenyl)-3-(3,4-dimethoxyphenyl)-1H-1,2,4-triazole (M.p. 184°–86° C.)

(E) 5-(2-hydroxymethylphenyl)-3-(3,4-methylenedioxyphenyl)-1H-1,2,4-triazole (M.p. 214°–16° C.)

We claim:

1. A 3,5-diphenyl-1H-1,2,4-triazole having the formula

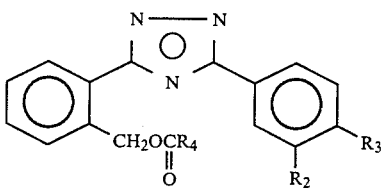

wherein
R$_2$ is methoxy or ethoxy;
R$_3$ is hydrogen, methyl, methoxy, ethoxy or when R$_2$ and R$_3$ are taken together represent a methylenedioxy group; and R$_4$ is an aliphatic saturated hydroxycarbyl group having from 5 to 14 carbon atoms.

2. A contragestational pharmaceutical composition suitable for subcutaneous or intramuscular injection containing from 1% to 10% (w/v) of a compound of claim 1, dissolved or suspended in a non-aqueous pharmaceutical vehicle.

3. A composition of claim 2 wherein the non-aqueous pharmaceutical vehicle is selected from the group consisting of oils of vegetable origin and the fat esters.

4. A method of terminating pregnancy in mammal which comprises the administration of a contragestational effective amount of a compound of claim 1 to a mammal in need thereof.

* * * * *